United States Patent
Slobozhanyuk et al.

(10) Patent No.: US 10,732,237 B2
(45) Date of Patent: Aug. 4, 2020

(54) MAGNETIC RESONANCE IMAGING MACHINE

(71) Applicant: Saint Petersburg National Research University of Information Technologies, Mechanics and Optics (ITMO UNIVERSITY), Saint Petersburg (RU)

(72) Inventors: Alexey Petrovich Slobozhanyuk, Saint Petersburg (RU); Aleksandr Nikitich Poddubnyj, Saint Petersburg (RU); Pavel Aleksandrovich Belov, Saint Petersburg (RU)

(*) Notice: Subject to any disclaimer, the term of this patent is extended or adjusted under 35 U.S.C. 154(b) by 0 days.

(21) Appl. No.: 15/739,121

(22) PCT Filed: Nov. 6, 2015

(86) PCT No.: PCT/RU2015/000746
§ 371 (c)(1),
(2) Date: Dec. 21, 2017

(87) PCT Pub. No.: WO2017/007365
PCT Pub. Date: Jan. 12, 2017

(65) Prior Publication Data
US 2018/0188339 A1     Jul. 5, 2018

(30) Foreign Application Priority Data
Jul. 3, 2015   (RU) ............... 2015126987

(51) Int. Cl.
*G01R 33/36*     (2006.01)
*G01R 33/34*     (2006.01)
(Continued)

(52) U.S. Cl.
CPC ........ *G01R 33/34092* (2013.01); *A61B 5/055* (2013.01); *G01R 33/36* (2013.01); *H01Q 15/00* (2013.01)

(58) Field of Classification Search
CPC ...... G01R 33/307; G01R 33/34; G01R 33/36; G01R 33/3607; G01R 33/3614;
(Continued)

(56) References Cited

U.S. PATENT DOCUMENTS

| | | | |
|---|---|---|---|
| 5,235,277 A | * | 8/1993 | Wichern ............. G01R 33/341 324/318 |
| 6,437,567 B1 | * | 8/2002 | Schenck .......... G01R 33/34061 324/318 |

(Continued)

FOREIGN PATENT DOCUMENTS

| CN | 102709705 A | 10/2012 |
|---|---|---|
| CN | 103585716 A | 2/2014 |

(Continued)

OTHER PUBLICATIONS

A.P. Slobozhanyuk et al., An Endoscope Based on Extremely Anisotropic Metamaterials for Applications in Magnetic Resonance Imaging, 59 J. Comm. Tech. & Elec. 562-570 (Jun. 2014). (Year: 2014).*

(Continued)

*Primary Examiner* — Tung X Nguyen
*Assistant Examiner* — Robert P Alejnikov, Jr.
(74) *Attorney, Agent, or Firm* — McDonnell Boehnen Hulbert & Berghoff LLP

(57) ABSTRACT

The invention relates to medical diagnostics and can be used in magnetic resonance imaging and magnetic resonance spectroscopy for increasing the quality of diagnostics of the internal organs of humans and animals. By virtue of a metamaterial, which is used as an electromagnetic field amplifier, being made from a set of advantageously oriented conductors, it becomes possible to spatially rearrange magnetic and electric fields operated at radio frequencies. In particular, in the examined object area, the radio frequency (Continued)

magnetic field is resonantly amplified, which makes it possible to increase the signal/noise ratio in MRI and to obtain better quality images and/or to perform the MRI examinations more quickly as there is no need to accumulate the signal. The proposed design of the metamaterial makes it possible to distance the radio frequency electric field from the area where the examined object is located, therefore enhancing safety of MRI scanning.

17 Claims, 2 Drawing Sheets

(51) Int. Cl.
  *A61B 5/055* (2006.01)
  *H01Q 15/00* (2006.01)
(58) Field of Classification Search
  CPC ............ G01R 33/3621; G01R 33/3628; G01R 33/3635; G01R 33/3642; G01R 33/365; G01R 33/3657; G01R 33/3664; G01R 33/3671; G01R 33/3678; G01R 33/3685
  USPC .......................................... 324/322
  See application file for complete search history.

(56) References Cited

U.S. PATENT DOCUMENTS

| | | | | |
|---|---|---|---|---|
| 2002/0180439 | A1* | 12/2002 | Lee ................... | G01R 33/3415 324/318 |
| 2009/0237077 | A1* | 9/2009 | Vaughan ............ | G01R 33/3415 324/307 |
| 2009/0309011 | A1* | 12/2009 | Ramahi ................ | B82Y 20/00 250/227.11 |
| 2011/0267061 | A1* | 11/2011 | Taracila ............. | G01R 33/3685 324/322 |
| 2013/0119987 | A1* | 5/2013 | Felmlee ........... | G01R 33/34092 324/322 |
| 2013/0119991 | A1* | 5/2013 | Soutome ................ | A61B 5/055 324/322 |

FOREIGN PATENT DOCUMENTS

| | | |
|---|---|---|
| JP | 2014-120989 A | 6/2014 |
| SU | 116247 U1 | 5/2012 |

OTHER PUBLICATIONS

International Search Report for PCT/RU2015/000746, dated Apr. 14, 2016, translated into English.
Written Opinion for PCT/RU2015/000746, dated Apr. 14, 2017, translated into English.
A.V. Shchelokova et al., "Usage of meta-resonators for improvement of magnetic resonance imaging," Proc. Int'l Conf. Days on Diffraction 2015, 380-82 (2015).
M.S. Khennouche et al., "Different configurations of metamaterials coupled with an RF coil for MRI applications," Appl. Phys. A, 109, 1059-63 (2012).

* cited by examiner

MAGNETIC RESONANCE IMAGING MACHINE

CROSS-REFERENCE TO RELATED APPLICATIONS

This application is a national stage application under 35 U.S.C. § 371 of International Application No. PCT/RU2015/000746, filed Nov. 6, 2015, which claims priority to Russian Patent Application No. 2015126987, filed Jul. 3, 2015, the disclosures of which are explicitly incorporated by reference herein.

TECHNICAL FIELD

This invention relates to the field of medical diagnostic screening and can be used in magnetic resonance imaging (MRI) and magnetic resonance spectroscopy (MRS) in order to improve the quality of diagnostic screening of human and animal internal organs.

PRIOR ART

MRI is currently one of the most informative methods for examining the internal organs of a human. The quality of an MR image and the size of the area of the patient which is being screened depend on the magnitude of induction of the magnetic field into which the patient is placed, and is also characterized by the magnitude of the signal-to-noise ratio, which depends partly on the parameters of the radio-frequency (RF) coils which are used to irradiate the area being screened using RF impulses and subsequently to receive the RF signal.

The level of the signal in an MRI machine depends on the strength of the static magnetic field of the system. Over the last two decades low-field imaging machines, operating with a static field of 1.5 tesla and below, have been used. Recently developed high-field systems with a static field of 3 tesla are already being successfully used in many hospitals in Russia, and worldwide. Ultra-high-field MRI machines, using a static field exceeding 3 tesla, are only permitted for scientific research and are not currently allowed to be used for the widespread scanning of patients. A higher static magnetic field makes it possible to significantly enhance the characteristics of an imaging machine, which is related to the fact that the greater the static field strength, the higher the operating frequency and the greater the signal-to-noise ratio [E. M. Haacke, R. W. Brown, M. R. Thompson, and R. Venkatesan, *Magnetic Resonance Imaging: Principles and Sequence Design*. (Wiley, 1999).]. The relationship between the signal-to-noise ratio and the RF parameters in MRI is determined approximately, as follows:

$$SNR \sim \frac{f^2 |(\sin(B_1^+ \gamma \tau) B_1^-)|}{(\sqrt{P_{abs}})}$$

where $\gamma$ is the gyromagnetic ratio, f is the frequency of the RF signal, r is the duration of the RF impulse, $B_1^+$ is the amplitude of the magnetic RF field, created by a source, said amplitude being responsible for the angle of inclination of the total magnetization vector for a given sequence of impulses, $B_1^-$ denotes the sensitivity of the receiving coil, while $P_{abs}$ is the total power absorbed by the sample.

Increasing the critically important signal-to-noise ratio makes it possible to obtain a sufficient level of signal from an encoded volume of much smaller size (increasing image resolution) or obtain an image of the same quality, but much faster by virtue of the fact that it is not necessary to accumulate the signal [J. M. Theysohn, O. Kraff, S. Maderwald, M. Schlamann, A. de Greiff, M. Forsting, S. Ladd, M. Ladd, and E. Gizewski, Hippocampus 19, 1 (2009)].

However, the use of high-field MRI machines is associated with a number of problems: 1) due to the small volume of acquired data, the effect of ultra-high-field MRI machines on the human body has not been studied, and many adverse effects (for example: dizziness and nausea) already manifest themselves when a patient is placed in an MRI machine having a field strength of 3 tesla [R. J. Stafford, Medical Physics 32, 2077 (2005)]; 2) many patients, with a variety of implants, are permitted to undergo scanning in imaging machines having a strength of 1.5 tesla, but scanning in 3-tesla imaging machines is forbidden [E. Kanal, A. J. Barkovich, C. Bell, et al, Journal of Magnetic Resonance Imaging 37, 501 (2013)]. Therefore, improving the characteristics of low-field MRI machines (in particular, increasing the signal-to-noise ratio) is a problem of critical importance.

The problem of ensuring safety in MRI machines is primarily determined by calculating the specific absorption coefficient, which indicates the quantity of absorbed electromagnetic energy, and consequently, the risk of tissue heating-up as a result of using RF impulses, which are required to obtain an MR signal. The specific absorption coefficient is proportionate to the square of the amplitude of the induced electrical field. In reality it is extremely important to minimize the RF electrical field in the area around the patient.

The efficiency of RF coils can be increased by using dielectric plates with high dielectric permittivity. In the paper [Q. X. Yang, J. Wang, J. Wang, C. M. Collins, C. Wang, M. B. Smith, Magn. Reson. Med. 65, 358 (2011)] it has been demonstrated that a material with high dielectric permittivity, positioned between RF coils and a subject, is capable of increasing the RF magnetic field. The disadvantages of such a technical solution include the relatively weak magnitude of overall amplification, which is due to the non-resonating nature of the plates, as well as the amplification of the electrical field around the patient.

The possibility of redistributing an RF magnetic field is described in the paper [M. J. Freire, R. Marques, & L. Jelinek, Appl. Phys. Lett. 93, 231108 (2008)]. Said paper shows that it is possible to develop special lenses made using a metamaterial, said lenses having negative magnetic permeability $\mu=-1$ at an operating frequency of a 1.5-tesla MR imaging machine. These types of lenses are capable of transmitting RF field distribution, present in the plane behind the lens, to any other equivalent plane in front of said lens, without loss of signal. Moreover, said paper shows that lenses made using metamaterials can be used as interface devices between an RF coil and a sample. The disadvantages of this type of lens, made using a metamaterial, include the existence of losses due to the influence of the substrate and electronic components, therefore a metamaterial lens can only be used if certain distances are maintained between the coil and the sample. Furthermore, the magnetic field distribution, in the area around the subject being examined, is relatively nonuniform due to the structure resolution. Moreover, local electrical field peaks are generated in the gaps between the lens elements.

The closest technical solution, accepted as the prior art, is a magnetic resonance imaging machine with a signal amplifier (patent CN102709705, published 3 Oct. 2012), consisting of a source of continuous magnetic field, a unit for generating a gradient magnetic field, a generator of radio-frequency impulses, a receiving device, as well as an electromagnetic field amplifier, provided in the form of a metamaterial, located between the subject being examined and the RF receiving coil. The metamaterial comprises an artificially created structure, consisting of at least one layer, which layer consists of elemental modules. The abovementioned microstructure modules consist of metal wires, made of a non-magnetic metal, on a dielectric substrate. The disadvantages of said device include acute dissipative losses which are associated with resonance in elemental modules which have been printed, including onto a substrate material made of FR4 polymer, as well as the fixed position of the device between the subject being examined and the receiving coil of the imaging machine, which limits the kinds of MRI scanning that can be conducted. Moreover, the metamaterial, described in this patent, as well as modifications thereof, described in patents by the same authors (patent CN103296465, published 11 Sep. 2013; patent CN103296446, published 11 Sep. 2013), do not allow RF electrical field distributions to be fully monitored, which may cause harm to the subject being examined.

SUMMARY OF THE INVENTION

The problem which the proposed invention is designed to solve, is to increase the sensitivity of magnetic resonance imaging machines and increase patient safety, as well as improve the quality of obtained images.

The problem of interest is solved by achieving a technical result, involving the redistribution of radio-frequency electrical and magnetic fields, which results in the level of the radio-frequency electrical field in the area around the patient being minimized, and the level of radio-frequency magnetic field being increased.

The indicated technical result is achieved by the fact that the magnetic resonance imaging machine, comprising at least a source of continuous magnetic field, a unit for generating a gradient magnetic field, a generator of radio-frequency impulses, a receiving device, as well as an electromagnetic field amplifier, provided in the form of a metamaterial, positioned close to a receiving device, is characterized in that the metamaterial includes a set of advantageously orientated extended conductors, which are isolated from each other, each of which is characterized by length $l_i$, said length having an average value equal to L, said conductors being positioned at distances $s_i$, relative to each other, with an average value equal to S, and having cross-sectional dimensions $d_i$, with an average value equal to D, wherein the average value of conductor lengths satisfies the requirement $0.4\lambda < L < 0.6\lambda$, where $\lambda$ is the wavelength of the radio-frequency signal in the metamaterial, the average value of distances between conductors satisfies the requirement $0.001\lambda < S < 0.1\lambda$, the average value of cross-sectional dimensions of the conductors satisfies the requirement $0.00001\lambda < D < 0.01\lambda$, and in that the conductors are manufactured from a non-magnetic metal. The electromagnetic field amplifier may be made in such a way that at least part of the metamaterial is located inside the dielectric, the end sections of the conductors may be provided with the capability of being cooled. The set of conductors may be positioned on a flat or a cylindrical surface.

Producing the metamaterial in the form of a set of advantageously orientated extended conductors, which are isolated from each other, the average length of which, L, lies within the range $0.4\lambda < L < 0.6\lambda$, where $\lambda$ is the wavelength of the radio-frequency signal in the metamaterial, satisfies the requirement of a resonator, the length of which satisfies the requirement for the emergence of half-wave resonance at the operating frequency of a specific MR imaging machine. In particular, at such a resonance the electromagnetic field, close to the resonator, is spatially distributed in such a way that an electric field node (zero point) is located in the center, said node coinciding with the magnetic field antinode (peak). By virtue of said electromagnetic field distribution, the specific energy absorption coefficient of the radio-frequency coil impulses is reduced, therefore the subject being examined, being located close to the center, experiences virtually no heating-up, while the local amplification of the RF magnetic field in this area makes it possible to improve the sensitivity of the RF coils and in this way increase the signal-to-noise ratio, having lowered the level of patient irradiation as a result of lowering the level of the electrical field.

The advantageous orientation of the conductors, the distance therebetween lying in the range $0.001\lambda < S < 0.1\lambda$, makes it possible to generate a uniformly distributed RF magnetic field in the spatial area around the subject being examined. The lower limit of this distance is determined based on practical considerations. Deviation from the non-uniformity of the RF magnetic field results in various levels of signal, obtained from various sections of one and the same material, which leads to the emergence of nonuniformity in the images of the subject being examined.

Conformance of the average value of cross-sectional dimensions of the conductors to the requirement $0.00001\lambda < D < 0.01\lambda$ makes it possible to obtain a greater signal-to-noise ratio value by increasing the resonator Q factor. The higher the resonator Q factor, the higher the field amplitude of the corresponding resonator mode and the lower the losses. The latter makes it possible to achieve a greater RF magnetic field amplitude and thereby increase the signal-to-noise ratio.

In order to ensure the safety of the patient the metamaterial conductors are manufactured using a non-magnetic metal, since MRI machines use a powerful static magnetic field, which when in contact with a number of metal compounds may lead to a "pulling-in" effect (a rapid attraction of objects to the center of the MRI tube). Moreover, the non-magnetic metal does not modify the static magnetic field and for that reason does not cause distortions of the MR images obtained.

Conductors may be partially placed into a dielectric in such a way, that only the ends of the conductors (spatial areas where electrical field peaks are positioned) are located inside the dielectric, which makes it possible to modify the electromagnetic field in such a way that the RF electrical field is pulled in to the material with the greater dielectric permittivity value, as a result of the fact that the dielectric acts as a condenser and additionally redistributes nearby fields. This fact makes it possible to further expand the safe zone, using a minimum electrical field value, up to any desired size. Research has shown that the best result is achieved if the edges of the conductors are placed into the dielectric such that the average length of the areas occupied by the dielectric, $L_\varepsilon$, made from a material with average dielectric permittivity $\varepsilon$ in the range $60 < \varepsilon < 100$, satisfies the requirement $0.04L < L_\varepsilon < 0.12L$.

Designing the device with partial or complete cooling of the conductors makes it possible to avoid undesired heating up of the metamaterial due to large-amplitude oscillating currents, caused by high-power RF impulses hitting the conductors.

Positioning of the metamaterial on flat or cylindrical surfaces depends on where, in which specific area of the imaging machine, amplification of the RF magnetic field needs to be performed, as a result of which the magnitude of the signal-to-noise ratio increases. When examining flat subjects (for instance a palm of a hand, or sole of a foot) a flat surface will be more suitable, for uniform amplification of the signal in this area. However, when examining curved subjects (for instance a head, or a torso) it is preferable that the conductors be positioned on cylindrical surfaces, making it possible to uniformly amplify the signal in the area being examined.

SUMMARY OF DRAWING FIGURES

The technical character of the invention being claimed is illustrated using figures.

Figure 1:
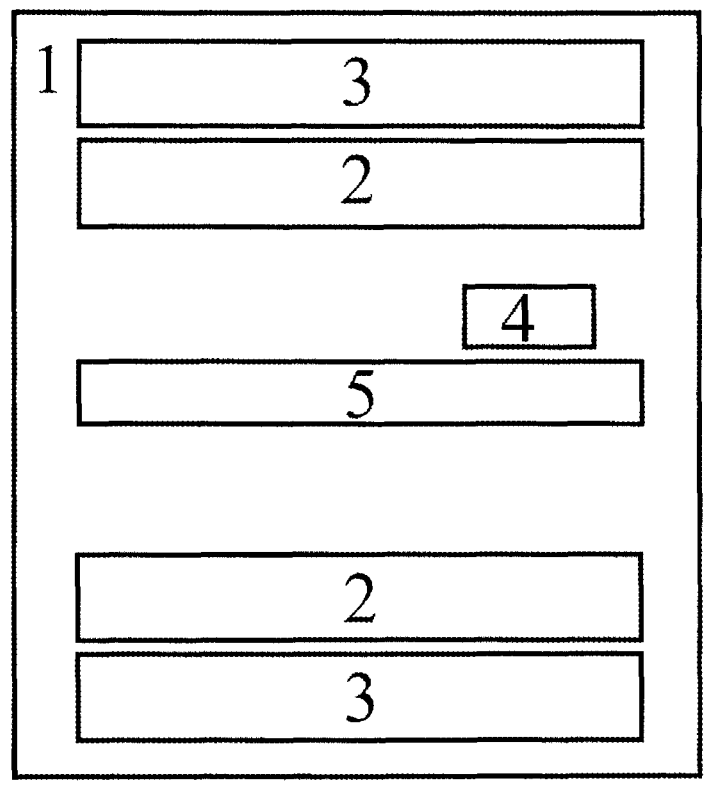
FIG. 1 shows the main layout of a magnetic resonance imaging machine.

The magnetic resonance imaging machine (FIG. 1) comprises a source of continuous magnetic field 1, a generator of radio-frequency impulses 2, a unit for generating a gradient magnetic field 3, a device for receiving radio-frequency signals 4, as well as an electromagnetic field amplifier 5, provided in the form of a metamaterial.

Figure 2:
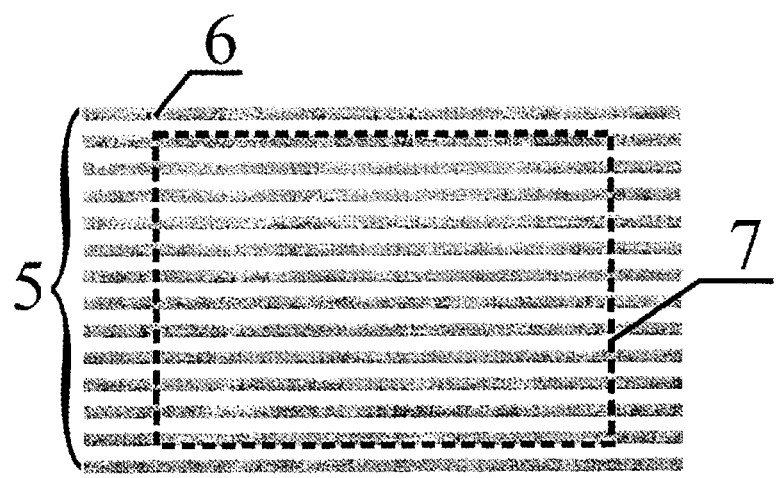
FIG. 2 shows one of the specific embodiments of an amplifier, made using metamaterial.

One of the embodiments of the electromagnetic field amplifier 5, provided in the form of a metamaterial, is shown in FIG. 2. Conductors 6 are positioned in parallel, on a flat surface. The average length of conductors 6 is equal to $L=0.5\lambda$, the average distance between conductors 6 is $S=0.02\lambda$, while the average cross section of conductors 6 is $D=0.004\lambda$. The subject being examined 7 is positioned on the metamaterial and is schematically shown as a rectangle.

EMBODIMENT OF THE INVENTION

The device works in the following way: using a source of continuous magnetic field 1 a powerful static magnetic field is created inside a magnetic resonance imaging machine, after which the subject being examined 7 is placed into the imaging machine. The magnetic moments of the protons of the subject being examined 7 align themselves parallel to the static magnetic field, the protons begin to precess at Larmor frequency, and the subject 7 acquires pronounced magnetization. Using the unit for generating a gradient magnetic field 3, additional magnetic fields are created, with said fields altering the magnitude of continuous magnetic field relative to the value, created by the source of continuous magnetic field 1, making it possible to encode the spectral and spatial response of certain lesser volumes of the subject being examined 7, said lesser volumes being characterized by their own period and frequency of Larmor precession. Then the subject being examined 7 is irradiated with an RF impulse created by the generator of radio-frequency impulses 2. Furthermore, the protons of the subject being examined 7 absorb the radiation energy, the precession frequency of said protons corresponding to the Larmor frequency. When radio-frequency signals hit the electromagnetic field amplifier 5, provided in the form of a metamaterial, local redistribution of radio-frequency fields takes place close to the subject being examined 7 by virtue of the fact that the length of each conductor 6 satisfies the requirement for the emergence of half-wave resonance, on which the RF magnetic field resonantly amplifies in the area around the subject being examined 7, and the RF electrical field is concentrated near to the edges of conductors 6, at a distance away from the subject being examined 7. In this way the amplitude of the RF magnetic field of generator 2 becomes amplified in the area around the subject being examined 7, making it possible to reduce the power level of the generator of radio-frequency impulses 2 and obtain the necessary RF magnetic field amplitude in the area around the subject being examined 7. Moreover, by virtue of the fact that the metamaterial redistributes the RF electrical field to a spatial area at a distance away from the subject being examined 7, it is possible to avoid undesired heating up of the subject being examined 7.

After the RF impulse stops, the protons of the subject being examined 7 start to revert to their original state, transmitting surplus energy in the form of RF waves. These waves are detected using a radio-frequency signal receiving device 4, and an MR image is obtained. When the parameters of the static magnetic field, the operating frequency of the imaging machine and the amplitude of the magnetic field of RF generator 2 are fixed, the signal-to-noise ratio is determined by the sensitivity of the receiving RF of receiving device 4. The electromagnetic field amplifier 5, provided in the form of a metamaterial, amplifies the sensitivity of RF receiving device 4 as a result of resonance amplification of the RF magnetic field, which makes it possible to increase the signal-to-noise ratio in the MRI.

Figure 3:
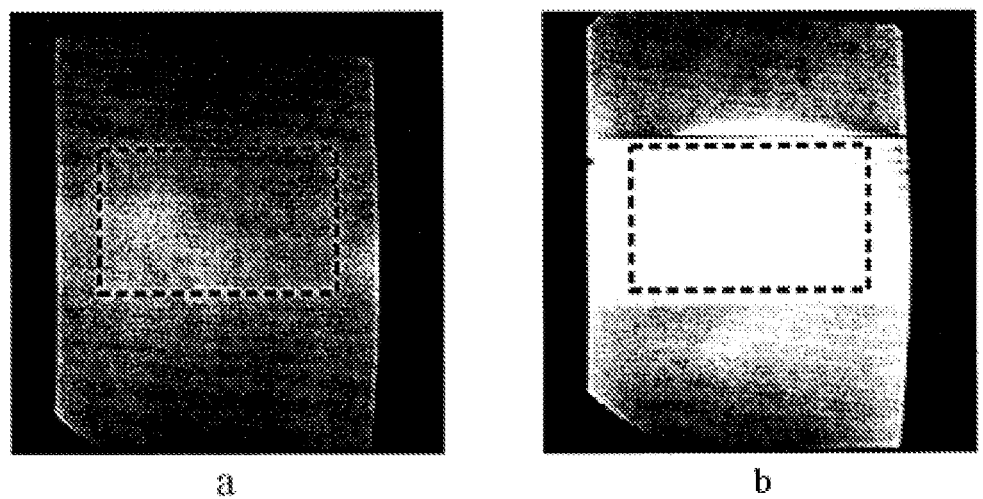
FIG. 3 shows the measured signal-to-noise ratio in the imaging machine, (a) without the electromagnetic field amplifier, provided in the form of metamaterial, and (b) with said amplifier.

FIG. 3 illustrates the measured signal-to-noise ratio (a) without electromagnetic field amplifier 5, provided in the form of a metamaterial, and (b) with said amplifier. The presence of the metamaterial makes it possible to amplify the signal-to-noise ratio by a factor of 2.7.

The invention claimed is:

1. A metamaterial device configured to operatively couple to a source of a Radio-Frequency, RF, signal having a wavelength, the metamaterial device comprising:
    a plurality of extended conductors each having a respective length that satisfies a half-wave resonance condition at the wavelength of the RF signal in the metamaterial device, wherein the extended conductors are arranged parallel to each other, wherein a respective length of each respective extended conductor is greater than a respective cross-sectional dimension of the respective extended conductor, wherein adjacent extended conductors of the plurality of extended conductors are spaced apart in a direction transverse to the respective lengths of the adjacent extended conductors, wherein the respective length of each adjacent extended conductor is greater than a distance between the adjacent extended conductors,
    the metamaterial device being configured to locally increase the magnetic field strength of the RF signal at the wavelength,
    wherein the plurality of extended conductors is at least partially located inside a dielectric material, wherein the dielectric material has a dielectric permittivity $\varepsilon$ greater than 60.

2. The metamaterial device of claim 1, wherein the plurality of extended conductors is supported by the dielectric material.

3. The metamaterial device of claim 1, wherein the extended conductors each comprise a non-magnetic metal.

4. The metamaterial device of claim 1, wherein the extended conductors of the plurality of extended conductors are electrically isolated from each other.

5. The metamaterial device of claim 1, wherein the respective length of each respective extended conductor is between 0.4 and 0.6 times the wavelength.

6. The metamaterial device of claim 1, wherein the respective cross-sectional dimension of each of the plurality of extended conductors is less than one hundredth of the wavelength.

7. The metamaterial device of claim 1, wherein the distance between the adjacent extended conductors is less than one tenth of the wavelength.

8. The metamaterial device of claim 1, wherein the distance between the adjacent extended conductors is greater than the cross-sectional dimension of each adjacent extended conductor.

9. The metamaterial device of claim 1, wherein end portions of the plurality of extended conductors are arranged to be cooled.

10. The metamaterial device of claim 1, wherein the plurality of extended conductors is arranged on a substantially flat surface.

11. The metamaterial device of claim 1, wherein the plurality of extended conductors is arranged on a substantially cylindrical surface.

12. A magnetic resonance imaging system for imaging an object, the system comprising:
an imaging region arranged to receive the object;
an RF transmitter coil arranged to generate a Radio-Frequency, RF, signal having a wavelength; and
a metamaterial device configured to operatively couple to the RF transmitter coil, wherein the metamaterial device comprises a plurality of extended conductors each having a respective length that satisfies a half-wave resonance condition at the wavelength of the RF signal in the metamaterial device, wherein the metamaterial device is configured to locally increase the magnetic field strength of the RF signal at the wavelength, wherein the metamaterial device is arranged between the imaging region and the RF transmitter coil such that the respective lengths of each extended conductor are oriented transverse to a direction from the RF transmitter coil to the imaging region,
wherein the plurality of extended conductors is at least partially located inside a dielectric material, wherein the dielectric material has a dielectric permittivity ε greater than 60.

13. The magnetic resonance imaging system of claim 12, wherein the extended conductors are arranged parallel to each other.

14. A method for imaging an object, the method comprising:
providing a metamaterial device operatively coupled to a generator of a Radio-Frequency, RF, signal having a wavelength, wherein the metamaterial device comprises a plurality of extended conductors each having a respective length that satisfies a half-wave resonance condition at the wavelength of the RF signal in the metamaterial device, the plurality of extended conductors being at least partially located inside a dielectric material having a dielectric permittivity ε greater than 60;
placing the object such that the metamaterial device is between the object and the generator of the RF signal, wherein the RF signal comprises an RF magnetic field component and an RF electric field component;
producing a magnetic field in the object;
irradiating the object with the RF signal such that the metamaterial device locally increases the RF magnetic field component of the RF signal in an area of the object to be imaged;
receiving a return RF signal from the object; and
obtaining an image of the object from the return RF signal.

15. The method of claim 14, wherein the metamaterial device locally decreases the RF electric field component of the electromagnetic signal in the area of the object to be imaged.

16. The method of claim 14, wherein the respective lengths of each extended conductor are oriented transverse to a direction from the generator to the imaging region.

17. The method of claim 14, wherein the extended conductors are arranged parallel to each other, wherein a respective length of each respective extended conductor is greater than a respective cross-sectional dimension of the respective extended conductor, wherein adjacent extended conductors of the plurality of extended conductors are spaced apart in a direction transverse to the respective lengths of the adjacent extended conductors, wherein the respective length of each adjacent extended conductor is greater than a distance between the adjacent extended conductors.

* * * * *